United States Patent [19]

Takahashi et al.

[11] 3,966,453
[45] June 29, 1976

[54] HERBICIDAL 2-HALO-4-TRIFLUOROMETHYL-4'-CYANOPHENYL-ETHERS

[75] Inventors: Ryohei Takahashi, Kusatsu; Kanichi Fujikawa, Kyoto; Isao Yokomichi, Kusatsu; Tadaaki Toki, Kusatsu; Shinzo Someya, Kusatsu, all of Japan

[73] Assignee: Ishihara Sangyo Kaisha Ltd., Osaka, Japan

[22] Filed: Mar. 25, 1975

[21] Appl. No.: 561,682

Related U.S. Application Data

[63] Continuation-in-part of Ser. No. 326,366, Jan. 24, 1973.

[30] Foreign Application Priority Data

Jan. 27, 1972    Japan.............................. 47-10367
May 13, 1972    Japan.............................. 47-47322
Aug. 2, 1972    Japan.............................. 47-76944
Dec. 6, 1972    Japan.............................. 47-121665
Dec. 11, 1972    Japan.............................. 47-123369

[52] U.S. Cl.................................. 71/105; 71/124; 260/465 F; 260/612 R; 260/613 R
[51] Int. Cl.².................... A01N 9/20; C07C 121/75
[58] Field of Search................... 260/465 F; 71/105

[56] References Cited
UNITED STATES PATENTS
3,766,238    10/1973    Rohr................................ 260/465

*Primary Examiner*—Elbert L. Roberts
*Assistant Examiner*—Dolph H. Torrence
*Attorney, Agent, or Firm*—Oblon, Fisher, Spivak, McClelland & Maier

[57] ABSTRACT

A herbicidal compound having the formula

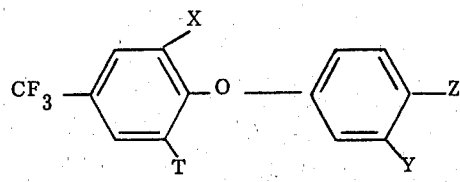

wherein X represents a halogen atom; T represents a hydrogen or a halogen atom; Y represents a hydrogen atom, a halogen atom, lower alkyl, or lower alkoxy group; and Z represents a halogen atom, or a cyano group.

7 Claims, No Drawings

HERBICIDAL 2-HALO-4-TRIFLUOROMETHYL-4'-CYANOPHENYL-ETHERS

CROSS REFERENCE TO RELATED APPLICATIONS

This is a Continuation-In-Part of Application Ser. No. 326,366 filed Jan. 24, 1973.

BACKGROUND OF THE INVENTION

1. Field of the Invention:

This invention relates to a class of herbicides which are effective for many agricultural uses.

2. Description of the Prior Art:

Some diphenylether type herbicides such as 2, 4-dichloro-4'-nitrodiphenyl ether, 2, 4, 6-trichloro-4'-nitrodiphenyl ether are known and have been practically used. In general, these herbicides have been considered to exhibit a more effective herbicidal effect by application in paddy fields rather than by dry fields. Also, more effective use of the herbicide is realized by treating soil rather than the stems and leaves of plants.

This invention is concerned with a class of diphenylether type compounds which have excellent herbicidal properties. These diphenylether herbicides exhibit remarkable herbicidal properties which are improvements over the properties of known diphenylether herbicides. These improvements are as follows:

1. The herbicides exhibit a remarkable growth inhibition of barnyard grass by treating the soil as well as the stems and leaves of the grass.
2. The herbicides exhibit excellent herbicidal properties against Slender spikerush, broad-leafed weeds, and the other various weeds.
3. The herbicides exhibit a remarkable genus-selective growth controlling effect on gramineous plants.
4. The herbicides can be effectively applied at low concentrations in paddy fields as well as dry fields.

SUMMARY OF THE INVENTION

One object of this invention is to provide herbicides which have improved herbicidal properties.

Another object of this invention is to provide a class of diphenylether compounds which are useful as herbicides.

These objects and other objects of this invention as hereinafter will become apparent can be attained by providing a herbicide which contains at least one active ingredient having the formula

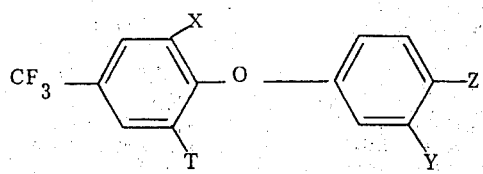

(I)

wherein X represents a halogen atom; T represents a hydrogen or a halogen atom; Y represents a hydrogen atom, a halogen atom, lower alkyl, or lower alkoxy group; and Z represents a halogen atom or a cyano group.

DESCRIPTION OF THE PREFERRED EMBODIMENTS

The active ingredients of this invention can be prepared by the following process. 2-halo-4-trifluoromethyl diphenylether having the formula

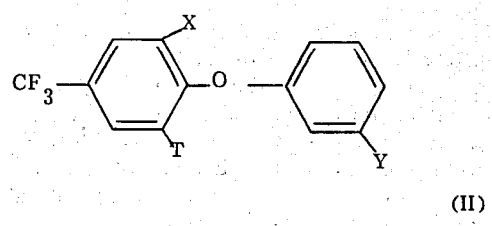

(II)

wherein X, T and Y are as defined in formula (I) above, is reacted with a nitrating agent or a halogenating agent to substitute a nitro group or a halogen atom in the 4' position to produce 4'-halogen substituted compounds with the structure of formula (I). Further, 4'-cyano substituted compounds with the formula (I) can be obtained by reducing above 4'-nitro substituted compound to yield the corresponding amino compound, which is diazotized. The diazonium compound is then subjected to a Sandmeyer or a Guttermann reaction.

2-Halo-4-trifluoromethyl diphenylether with the formula (I) or (II) can be prepared by reacting 1, 2-dihalo-4-trifluoromethyl benzene having the formula

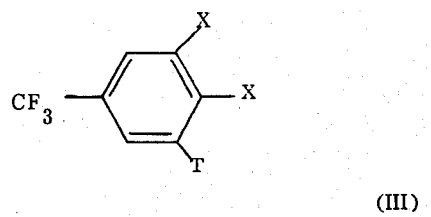

(III)

with a phenol having the formula

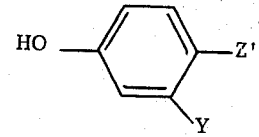

(IV)

wherein X, T and Y are defined as in formula (I) above and Z' is a hydrogen atom, a halogen atom or a cyano group in the presence of an alkaline compound. Suitable alkaline compounds useful for this reaction include an alkali metal hydroxide, or carbonate such as sodium hydroxide, sodium carbonate, potassium carbonate, and the like.

In the reaction of compound (III) with compound (IV), it is preferable to add a non-protonic polar solvent and a copper catalyst. Suitable solvents include dimethylsulfoxide, dimethylformamide, dimethylacetamide, N-methylpyrrolidone, hexamethyl phosphoramide or sulfolane. Suitable copper catalysts include copper powder, a copper-zinc mixture, cupric chloride, cuprous chloride, cupric oxide, cuprous oxide, cupric sulfate, cuprous bromide, and the like.

Generally, the reaction can be smoothly performed at temperatures higher than 100°C. If the reaction temperature is too high, disadvantageous side reactions occur or the product obtained is colored. Accordingly, it is preferable to react the compounds at 130° – 200°C., especially 140° – 180°C.

Examples of the preparation of certain active ingredients of this invention are illustrated and are not intended to be limiting unless otherwise specified.

PREPARATION 1

2, 6, 4'-trichloro-4-trifluoromethyl-3'-methoxydiphenyl ether

A 3.4 g (0.01 mole) quantity of 2, 6-dichloro-4-trifluoromethyl-3'-methoxydiphenyl ether was placed into a 50 ml four-necked flask equipped with a stirrer, a dropping funnel, a thermometer and a condenser and 20 ml of glacial acetic acid was added to the flask to dissolve the diphenylether. This was followed by the dropwise addition of 8.4 g of 10% acetic acid solution containing chlorine. The flask was heated to about 40°C., and the contents were reacted for 2 hours with stirring. After completion of the reaction, the contents of the flask were placed in a beaker filled with a suitable amount of water, and were extracted with ether. The effluent was washed with water and dried with calcium chloride overnight. After drying, the effluent was filtered. The filtrate was condensed and then distilled under a reduced pressure to yield 3.0 g of the product having a boiling point of 156° – 158°C/4mmHg.

PREPARATION 2

2-bromo-4-trifluoromethyl-4'-cyanodiphenylether

A 2.8 g (0.01 mole) quantity of 2-amino-4-trifluoromethyl-4'-cyanodiphenylether was placed into the 50 ml four-necked flask of Preparation 1, and 25 ml of flacial acetic acid was added to the flask to dissolve the diphenyl ether. A 3.5 ml (0.02 mole) amount of 47% hydrobromic acid was added to the flask, and it was cooled to a temperature lower than 0°C. A 7 g (0.01 mole) amount of 10% aqueous solution of sodium nitrate was added dropwise, with the subsequent addition of 3.6 g (0.03 mole) of potassium bromide. The flask was heated slowly and a suitable amount of copper powder was added to the reaction solution at 50°C. for 30 minutes to generate nitrogen gas. After the reaction, the contents of the flask were placed into a beaker filled with a suitable amount of water and were extracted with ether. The effluent was washed with water and dried with calcium chloride overnight. After drying, the effluent was filtered, and the filtrate was concentrated and distilled under a reduced pressure to yield 1.4 g of the product having a boiling point of 135° – 139°C/1mmHg.

The active ingredients of the herbicides of this invention and the physical properties thereof are shown in Table 1. The active ingredients were prepared by the previously described processes.

TABLE 1

| Active Ingredient No. | Active Ingredient diphenylether | Physical properties |
|---|---|---|
| 1 | 2,4'-dichloro-4-trifluoromethyl diphenylether | b.p. 129–132°C/4.8 mmHg |
| 2 | 2-chloro-4-trifluoromethyl-4'-bromodiphenylether | b.p. 151.5–152°C/3.2 mmHg |
| 3 | 2,4'-dichloro-4-trifluoromethyl-3'-methoxydiphenylether | m.p. 98–106°C |
| 4 | 2,4'-dichloro-4-trifluoromethyl-3'-ethoxydiphenylether | b.p. 157–158°C/3 mmHg |
| 5 | 2,4'-dichloro-4-trifluoromethyl-3'-n-propoxydiphenylether | b.p. 159–160°C/3 mmHg |
| 6 | 2,4'-dichloro-4-trifluoromethyl-3'-n-butoxydiphenylether | b.p. 162–164°C/3 mmHg |
| 7 | 2-chloro-4-trifluoromethyl-3'-methoxy-4'-bromodiphenylether | b.p. 161–162°C/2.6 mmHg |
| 8 | 2-chloro-4-trifluoromethyl-3'-ethoxy-4'-bromodiphenylether | b.p. 168–169°C3 mmHg |
| 9 | 2, 4'-dichloro-4-trifluoromethyl-3'-methyldiphenylether | b.p. 135–137°C/1 mmHg |
| 10 | 2, 3', 4'-trichloro-4-trifluoromethyl diphenylether | b.p. 147°C/0.6 mmHg |
| 11 | 2-chloro-4-trifluoromethyl-4'-cyanodiphenylether | b.p. 133–137°C/1 mmHg |
| 12 | 2-chloro-4-trifluoromethyl-3'-methyl-4'-cyanodiphenylether | b.p. 171–175°C/1.5 mmHg |
| 13 | 2-chloro-4-trifluoromethyl-3'-methoxy-4'-cyanodiphenylether | m.p. 90–91.5°C |
| 14 | 2-chloro-4-trifluoromethyl-3'-ethoxy-4'-cyanodiphenylether | m.p. 101–104°C |
| 15 | 2-chloro-4-trifluoromethyl-3'-n-propoxy-4'-cyanodiphenylether | b.p. 173–175°C/1 mmHg |
| 16 | 2-chloro-4-trifluoromethyl-3'-isopropoxy-4'-cyanodiphenylether | b.p. 175–180°C/3 mmHg |
| 17 | 2-chloro-4-trifluoromethyl-3'-n-butoxy-4'-cyanodiphenylether | b.p. 205–210°C/2.5 mmHg |

TABLE 1-continued

| Active Ingredient No. | Active Ingredient diphenylether | Physical properties |
|---|---|---|
| 18 | 2-bromo-4-trifluoromethyl-4'-chlorodiphenylether | b.p. 108–111°C/1 mmHg |
| 19 | 2-bromo-4-trifluoromethyl-3'-methoxy-4'-chlorodiphenylether | b.p. 137–140°C/0.5 mmHg |
| 20 | 2-bromo-4-trifluoromethyl-3'-ethoxy-4'-chlorodiphenylether | b.p. 145–155°C/2 mmHg |
| 21 | 2-bromo-4-trifluoromethyl-4'-cyanodiphenylether | b.p. 135–139°C/1 mmHg |
| 22 | 2-iodo-4-trifluoromethyl-3'-ethoxy-4'-bromodiphenylether | b.p. 215–220°C/3.5 mmHg |
| 23 | 2,6,4'-trichloro-4-trifluoromethyldiphenylether | b.p. 132–134°C/5.6 mmHg |
| 24 | 2,6-dichloro-4-trifluoromethyl-4'-cyanodiphenylether | m.p. 87–91°C |
| 25 | 2,6,4'-trichloro-4-trifluoromethyl-3'-methoxydiphenylether | b.p. 156–158°C/4 mmHg |
| 26 | 2,6-dichloro-4-trifluoromethyl-3'-methoxy-4'-bromodiphenylether | b.p. 170–173°C/3 mmHg |
| 27 | 2,6-dichloro-4-trifluoromethyl-3'-ethoxy-4'-bromodiphenylether | b.p. 179–183°C/3.5 mmHg |
| 28 | 2,6-dichloro-4-trifluoromethyl-3'-methoxy-4'-cyanodiphenylether | m.p. 146–149°C |
| 29 | 2,6-dichloro-4-trifluoromethyl-3'-ethoxy-4'-cyanodiphenylether | m.p. 90–93°C |
| 30 | 2-chloro-4-trifluoromethyl-3',4'-difluorodiphenyl-ether | 127–133°C/5 mmHg |

Having generally described the invention, a further understanding can be obtained by reference to certain specific examples which are provided herein for purposes of illustration only and are not intended to be limiting unless otherwise specified.

EXPERIMENT 1

Each pot of 1/10,000 are was filled with soil and the soil was super-saturated with water. A specific amount of an air-dried edible barnyard grass seed was sown in the pot and covered with soil. When the barnyard grass appeared on the surface of the soil, water was poured into each pot to a depth of 3 cm and then an aqueous dispersion of one of the active ingredients of this invention was poured into the pot. Fourteen days after this treatment, the grass which had survived was cut, air dried and weighed. The results are shown in Table II in percent by weight of the grass which survived from the treated seed versus the untreated seed, and are indicated as "Degree of Growth".

TABLE II

| Test No. | Active ingredient No. | (are=100 m²) Degree of Growth (%) Amount of active ingredient | |
|---|---|---|---|
| | | 20 (g are) | 10(g/are) |
| 1 | 4 | 0 | 0 |
| 2 | 7 | 0 | 2 |
| 3 | 8 | 0 | 0 |
| 4 | 9 | 0 | 0 |
| 5 | 10 | 0 | 4 |
| 6 | 11 | 0 | 0 |
| 7 | 12 | 0 | 0 |
| 8 | 13 | 0 | 0 |
| 9 | 14 | 0 | 0 |
| 10 | 15 | 0 | 0 |
| 11 | 16 | 0 | 0 |
| 12 | 17 | 0 | 0 |
| 13 | 19 | 0 | 0 |
| 14 | 20 | 0 | 1 |
| 15 | 21 | 0 | 0 |

TABLE II-continued

| Test No. | Active ingredient No. | (are=100 m²) Degree of Growth (%) Amount of active ingredient | |
|---|---|---|---|
| | | 20 (g are) | 10(g/are) |
| 16 | 23 | 0 | 0 |
| 17 | 24 | 0 | 0 |
| 18 | 25 | 0 | 0 |
| 19 | 26 | 0 | 0 |
| 20 | 28 | 0 | 0 |
| 21 | 29 | 0 | 0 |
| 22 | 30 | 0 | 0 |
| 23 | (reference) 2-chloro-4-trifluoromethyl-3'-methoxy diphenyl ether | 73 | 85 |
| 24 | (reference) 2,2'-dichloro-4-trifluoromethyl diphenylether | 71 | 82 |
| 25 | (reference) 2-bromo-4-trifluoromethyl-3'-methoxy diphenylether | 65 | 94 |
| 26 | (reference) 2-chloro-4-trifluoromethyl-2'-methyl diphenylether | 85 | 97 |
| 27 | (reference) 2,6-dichloro-4-trifluoromethyl diphenyl ether | 75 | 92 |

EXPERIMENT 2

The procedure of Experiment 1 was followed excep that water was poured to a depth of 4 cm at the two lea stage of plant growth. Eighteen days after treatmen with the specified ingredients, tests were made. Th results are shown in Table III.

TABLE II TABLE III

| | | Degree of Growth (%) | | |
|---|---|---|---|---|
| | (are=100 m²) | Amount of active ingredient (g/are) | | |
| Test No. | Active ingredient No. | 20 | 10 | 5 |
| 1 | 8 | 0 | 0 | |
| 2 | 9 | 0 | 7 | |
| 3 | 11 | 0 | 0 | |
| 4 | 12 | 0 | 0 | 0 |
| 5 | 13 | 0 | 0 | 0 |
| 6 | 14 | 0 | 0 | 0 |
| 7 | 16 | 0 | 0 | 0 |
| 8 | 19 | 1 | 1 | |
| 9 | 21 | 0 | 0 | |
| 10 | (reference) 2,4,6-trichloro-3'-methoxy-4'-nitrodiphenylether | 88 | 97 | |
| 11 | (reference) 2-trifluoromethyl-4-chloro-3'-methoxy-4'-nitrodiphenylether | 100 | 100 | |

EXPERIMENT 3

Each deep vat of 1/3,000 are was filled with soil and the soil was supersaturated with water. Seeds of broad-leafed weeds such as Monochoria, Toothcup, and Slender spikerush, were placed in respective vats at a depth of about 5 mm. Water was poured into each vat to a depth of 3 cm. After the weeds had emerged, an aqueous dispersion of each active ingredient of this invention was sprayed onto the weeds. Fourteen days after this treatment, the Slender, pikerush and broad-leafed weeds which had survived were observed. The results are shown in Table IV. In the Table, the degree of growth control is shown as it relates to the following standards:

5: Complete growth suppression is found
4: Remarkable growth suppression is found
3: Clear growth suppression compared with untreated plants is found
2: Slight growth suppression is found
1: No apparent difference between treated and untreated plants

TABLE IV

| Broad-leafed weeds | | BL | | |
| Slender spikerush | | SL | | |
| | | (are = 100 m²) | | |
| Active ingredient No. | Weed | Degree of Growth Control | | |
| | | Amount of active ingredient (g/are) | | |
| | | 10 | 5 | 5 |
| 12 | BL | 5 | 5 | 5 |
| | SL | 5 | 5 | 5 |
| 13 | BL | 5 | 5 | 5 |
| | SL | 5 | 5 | 5 |
| 14 | BL | 5 | 5 | 5 |
| | SL | 5 | 5 | 5 |
| 15 | BL | 5 | 5 | 5 |
| | SL | 5 | 5 | 5 |
| 16 | BL | 5 | 5 | 4–5 |
| | SL | 5 | 5 | 4 |
| 17 | BL | 5 | 5 | 5 |
| | SL | 5 | 5 | 5 |

EXPERIMENT 4

The method of Experiment 2 was repeated except that seeds of rice and air dried edible barnyard grass were sown. At the 1.5 leaf stage of growth of the barnyard grass, water was poured and the active ingredients were sprayed onto the plants. The results are shown in Table V.

TABLE V

| | | | (are = 100 m²) | |
| Test No. | Active ingredient No. | Amount of active ingredient [g/are] | Degree of Growth [%] | |
| | | | rice | plant edible barnyard grass |
| 1 | 11 | 20 | 80 | 0 |
| | | 10 | 100 | 0 |
| 2 | 19 | 20 | 100 | 0 |
| | | 10 | 100 | 4 |
| 3 | 21 | 20 | 100 | 0 |
| | | 10 | 100 | 0 |
| 4 | 25 | 20 | 70 | 0 |
| | | 10 | 70 | 0 |

EXPERIMENT 5

Each pot of 1/900 are was filled with soil containing general up-land weed seeds such as wild barnyard grass, bog stitch-wort, lawn grass, wavy bittercress, polygonum species, large crab-grass, etc. to a depth of about 2 cm. Three days after sowing, a specific amount of an aqueous dispersion of each ingredient was sprayed onto the soil. Ten days after application of the ingredients, the growth condition of each of the plants and weeds was observed. The results are shown in Table VI and VII.

TABLE VI

| | | | (are = 100 m²) | | | | | |
| Test No. | Active ingredient | Amount of active ingredient [g/are] | Degree of Growth Control | | | | | |
| | | | Weed | | | | | |
| | | | ① | ② | ③ | ④ | ⑤ | ⑥ |
| 1 | 4 | 100 | 5 | 5 | 5 | 5 | 4–5 | 5 |
| | | 50 | 5 | 5 | 5 | 5 | 4–5 | 5 |
| 2 | 7 | 100 | 5 | 5 | 5 | 5 | 5 | 5 |
| | | 50 | 4–5 | 5 | 5 | 5 | 4 | 5 |
| 3 | 8 | 100 | 5 | 5 | 5 | 5 | 5 | 5 |
| | | 50 | 4–5 | 5 | 5 | 5 | 4 | 5 |
| 4 | 10 | 100 | 4–5 | 5 | 5 | 5 | 4–5 | 5 |
| | | 50 | 4 | 4 | 5 | 5 | 4 | 5 |
| 5 | 11 | 100 | 5 | 5 | 5 | 5 | 5 | 5 |
| | | 50 | 5 | 5 | 5 | 5 | 5 | 5 |
| 6 | 19 | 100 | 4–5 | 5 | 5 | 5 | 4–5 | 5 |
| | | 50 | 4 | 4 | 5 | 5 | 4 | 5 |
| 7 | 23 | 100 | 5 | 5 | 5 | 5 | 5 | 5 |
| | | 50 | 4 | 5 | 5 | 5 | 4 | 5 |
| 8 | 25 | 100 | 5 | 5 | 5 | 5 | 5 | 5 |
| | | 50 | 5 | 5 | 5 | 5 | 4–5 | 5 |
| 9 | 26 | 100 | 5 | 5 | 5 | 5 | 4–5 | 5 |
| | | 50 | 4 | 5 | 5 | 4–5 | 4 | 5 |
| 10 | 30 | 100 | 4–5 | 5 | 5 | 4 | 4 | 5 |
| | | 50 | 4 | 4 | 5 | 4 | 4 | 5 |

TABLE VII (are = 100 m²)

| Test No. | Active ingredient | Amount of active ingredient [g/are] | Degree of Growth Control Weed ① | ② | ③ | ④ |
|---|---|---|---|---|---|---|
| 1 | 11 | 20 | 5 | 5 | 5 | 5 |
|   |    | 10 | 5 | 5 | 5 | 5 |
| 2 | 13 | 20 | 5 | 5 | 5 | 5 |
|   |    | 10 | 5 | 5 | 5 | 5 |
| 3 | 14 | 20 | 5 | 5 | 5 | 5 |
|   |    | 10 | 5 | 5 | 5 | 5 |
| 4 | 15 | 20 | 5 | 5 | 5 | 5 |
|   |    | 10 | 5 | 5 | 5 | 5 |
| 5 | 16 | 20 | 5 | 5 | 5 | 5 |
|   |    | 10 | 5 | 5 | 5 | 5 |
| 6 | 17 | 20 | 3–4 | 3–4 | 5 | 5 |
|   |    | 10 | 3 | 3–4 | 5 | 5 |
| 7 | 21 | 20 | 5 | 4–5 | 5 | 5 |
|   |    | 10 | 4 | 4 | 4 | 4 |

| 1 | Wild barnyard grass | 4 | Large crab-grass |
| 2 | Bog stitch-wort | 5 | Lawn grass |
| 3 | Wavy bittercress | 6 | Polygonum species |

EXPERIMENT 6

Each pot of 1/5,000 are was filled with soil and predetermined amounts edible barnyard grass seeds were sown and the seeds were covered with soil. When the barnyard grass had grown to the two-leaf stage, a specific amount (15 l/lare) of an aqueous dispersion of each ingredient was sprayed onto the stems and leaves. Ten days after the application of the ingredients, the growth condition of the barnyard grass was observed. The results are shown in Table VIII.

TABLE VIII

| Test No. | Active ingredient No. | Degree of Growth Control Concentration of active ingredient [ppm] | |
|---|---|---|---|
|   |   | 2000 | 1000 |
| 1 | 11 | 5 | 4 |
| 2 | 12 | 5 | 5 |
| 3 | 13 | 5 | 4–5 |
| 4 | 14 | 5 | 5 |
| 5 | 15 | 5 | 4 |
| 6 | 16 | 5 | 5 |
| 7 | 17 | 5 | 3–4 |
| 8 | 21 | 4 | 4 |

It is clear from the experimental tests that when the active ingredients of this invention are used as herbicides, the following advantages are found which makes their use suitable as herbicides.

1. They are remarkably high growth suppression effects against barnyard grass in paddy fields or in dry fields by application to the soil as well as by application to the stems and leaves of plants.

2. They have an excellent herbicidal affect on various weeds in paddy fields as well as in dry fields.

3. Excellent affects can be obtained in dry fields in low concentration.

4. The activity of the ingredients is high even when diluted, so that they can be applied in low concentrations.

The herbicides of this invention can be applied in various places such as paddy fields, dry lands, orchards, mulberry farms, forests, ridges, grounds, factory sites. Several suitable methods of application can be used which include application under flooded conditions, direct application to the soil or to the stems and leaves of plants. The herbicidal compounds can be applied in the form of an aqueous dispersion, a dust, a granule, a wettable powder, a water miscible solution or an emulsion with auxiliary agents such as a diluent, a solvent, an emulsifier and a spreader. The herbicidal compounds of this invention may be used together with other herbicidal compounds, insecticides, fungicides, fertilizers or soil.

The quantity of herbicide of this invention required depends upon the weather, soil, form of preparation of the agent, the season, method of application and type of weeds treated. Usually the active ingredients are applied in the range of 0.5 – 100 g/are, preferably 2.5 – 50 g/are.

| PREPARATION OF COMPOSITION 1 | |
|---|---|
| 2,6-dichloro-4-trifluoromethyl-3'-ethoxy-4'-cyanodiphenylether | 5 wt. part |
| bentonite | 90 wt. part |
| sodium lignin sulfonate | 5 wt. part |

The components listed above were mixed and granulated with water to form the herbicidal composition (granules).

| PREPARATION OF COMPOSITION 2 | |
|---|---|
| 2-chloro-4-trifluoromethyl-3'-methoxy-4'-cyanodiphenylether | 15 wt. part |
| polyoxyethylene stearate | 20 wt. part |
| xylene | 65 wt. part |

The components listed above were mixed to form a solution of the herbicide (emulsion type).

| PREPARATION OF COMPOSITION 3 | |
|---|---|
| 2-chloro-4-trifluoromethyl-3'-ethoxy-4'-cyanodiphenylether | 40 wt. part |
| kaoline powder | 55 wt. part |
| sodium alkylbenzenesulfonate | 5 wt. part |

The components listed above were uniformly mixed to form the herbicide (wettable powder).

| PREPARATION OF COMPOSITION 4 | |
|---|---|
| 2,4'-dichloro-4-trifluoromethyl-3'-methoxy diphenylether | 15 wt. part |
| polyoxyethylene stearate | 20 wt. part |
| xylene | 65 wt. part |

The components listed above were mixed to form a solution of the herbicide (emulsion type).

Other active ingredients were admixed with auxiliary agents in accordance with the formula above to obtain herbicidal compositions.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A compound having the formula:

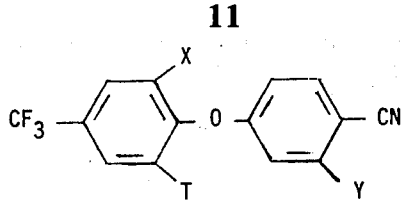

wherein X represents a halogen atom, T represents a hydrogen or a halogen atom, and Y represents a hydrogen atom, halogen atom, lower alkyl, lower alkoxy group.

2. The compound of claim 1, wherein Y is a hydrogen atom.

3. The compound of claim 1, wherein Y is a halogen atom.

4. The compound of claim 1, wherein Y is lower alkyl group.

5. The compound of claim 1, wherein Y is lower alkoxy group.

6. The compound of claim 1, wherein X is chlorine atom, and Y is lower alkoxy group.

7. The method of killing weeds which comprises applying a herbicidally effective amount of a compound of claim 1.

* * * * *